United States Patent [19]

Rojey et al.

[11] Patent Number: 4,873,835

[45] Date of Patent: Oct. 17, 1989

[54] PROCESS FOR THE SIMULTANEOUS EXCHANGE OF HEAT AND MATTER THROUGH A POROUS WALL

[75] Inventors: Alexandre Rojey, Garches; Alain Grehier, Paris, both of France

[73] Assignee: Institut Francais du Petrole, Rueil-Malmaison, France

[21] Appl. No.: 143,097

[22] Filed: Jan. 12, 1988

[30] Foreign Application Priority Data

Jan. 13, 1987 [FR] France ............................... 87 00359

[51] Int. Cl.$^4$ ............................................. B01D 53/22
[52] U.S. Cl. ........................................ 62/93; 62/268; 62/270; 55/16; 55/80; 55/269; 165/111; 165/907
[58] Field of Search ........................ 55/16, 80, 81, 209, 55/269, DIG. 42; 165/111, 907; 62/93, 268, 270

[56] References Cited

U.S. PATENT DOCUMENTS

| | | | |
|---|---|---|---|
| 2,478,617 | 8/1949 | Anderegg | 62/93 |
| 3,420,069 | 1/1969 | Booth | 62/268 |
| 4,040,804 | 8/1977 | Harrison | 55/158 |

FOREIGN PATENT DOCUMENTS 402722 10/1973 U.S.S.R. ................................. 62/93

*Primary Examiner*—Albert W. Davis, Jr.
*Attorney, Agent, or Firm*—Millen, White & Zelano

[57] ABSTRACT

The invention relates to a process for the simultaneous exchange of heat and matter through a porous wall. A relatively hot gaseous mixture of two constituents passes through an exchange compartment by flowing along the first surface of a porous wall and is progressively cooled, which causes the condensation of a fraction of said mixture. This fraction is vaporized on the second surface of the wall in contact with a relatively cold gas. This process is useful for the fractionation of a mixture of two constituents of a gas, for example, of a mixture of pentane and heptane.

20 Claims, 2 Drawing Sheets

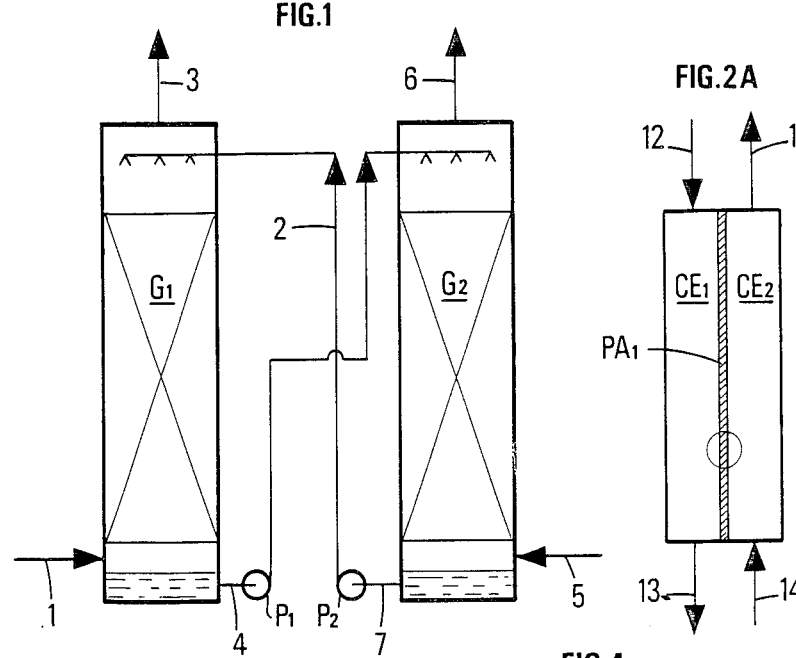
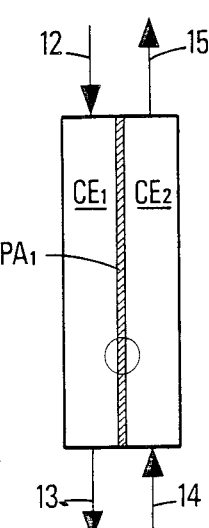
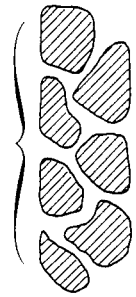
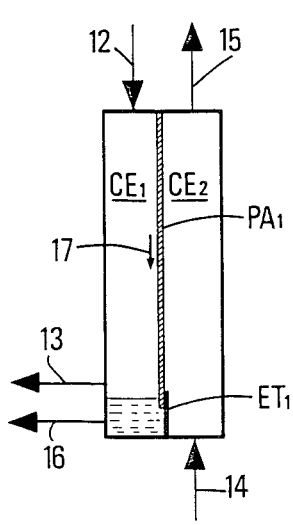
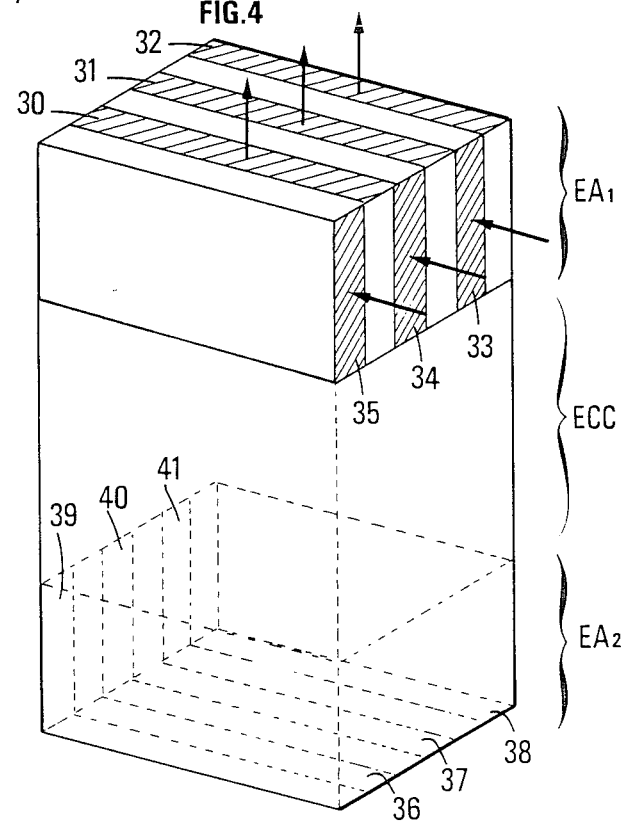
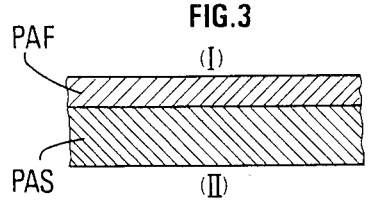

PROCESS FOR THE SIMULTANEOUS EXCHANGE OF HEAT AND MATTER THROUGH A POROUS WALL

BACKGROUND OF THE INVENTION

The process according to the invention applies to the simultaneous exchange of heat and matter.

It can be used particularly for effecting exchange between hot and moist gas which is cooled by transferring heat and condensed water to a colder and dryer gas which becomes charged with steam in being heated.

Such simultaneous exchange of heat and of matter has already been done in different ways in the prior art.

FIG. 1 shows a first known method of operating.

A hot and moist gas arrives through the pipe 1 into a packed column G1 in which it is contacted with a flow of colder water arriving through the pipe 2. The gas emerges cooled through the pipe 3. The cooling causes an additional condensation of water which is removed through the pipe 4 and is taken up by the pump P1 at the same time as the cooling water at the bottom of the packed column G1.

The water thus heated is contacted in a packed column G2 with a colder and dryer gas which arrives through the pipe 5. The gas emerges heated through the pipe 6 becoming charged with water in the course of the contact which took place in the packed column G2.

The water collected at the bottom of the packed column G2 is removed through the pipe 7 and is taken up by the pump P2.

This device has the drawback of being cumbersome and requiring two circulating pumps.

It has been discovered that it is possible to avoid these drawbacks by using the process according to the invention.

This process of simultaneous transfer of heat and of matter from a relatively hot gaseous phase (I) to a relatively cold gaseous phase (II), the gaseous phase (I) comprising at least two constituents A and B having different condensation temperatures, the condensation temperature of A being lower than the condensation temperature of B and at least the constituent B being at least in part condensable under the conditions of the process, is characterized in that the gaseous phase (I) is circulated in contact with the first surface of an exchange wall permeable at least to the constituent B in the liquid state, in that the gaseous phase (II) is circulated in contact with the second surface of the porous exchange wall, in a direction substantially parallel and opposite that of the flow of the gaseous phase (I), the temperature of the gaseous phase (II) at the start of the contact being sufficiently low to permit the condensation of at least one fraction of the constituent B of the gaseous phase (I) and the maintenance of the resulting condensate in at least a part of the thickness of the porous part of the exchange wall, the temperature of the gaseous phase (II) not however being too low to avoid a total condensation of the constituents A and B of said gaseous phase (I) in the course of said contact, the pressure conditions on each side of the wall being mutually adapted to permit said condensation of a fraction of the constituent B on said first surface and the vaporisation of said condensed fraction on said second surface, and in that the gaseous phase (I) of lower temperature of lowered concentration of constituent B and of increased concentration of constituent A, and the gaseous phase (II) of increased temperature and concentration in constituent B, are withdrawn separately.

BRIEF DESCRIPTION OF THE DRAWINGS

FIG. 1 is a diagram of the prior art;
FIG. 2A is a diagram of the invention;
FIG. 2B is an enlargement of the wall shown diagramatically;
FIG. 2C is a diagram of a further embodiment;
FIG. 3 is an enlargement of a further embodiment of the wall;
FIG. 4 is a diagram of a multiple channel embodiment.

Figure 5:
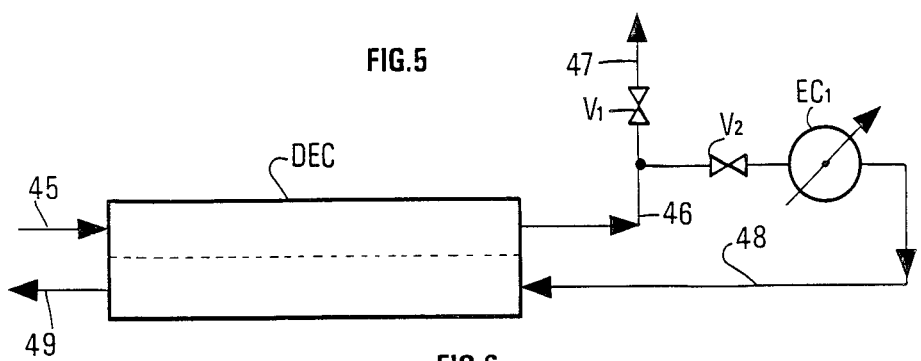
FIG. 5 is a diagram of a use of the invention.

The principle of the process is described in relation with the diagram of FIG. 2A.

A gaseous phase (I) comprising at least two constituents A and B arrives through the pipe 12 in an exchange compartment CE1 separated from a second exchange compartment CE2 by an exchange wall PA1 comprising a network of pores communicating with one another and opening on each side of the wall in a configuration such as that which is shown diagramatically in FIG. 2B.

The gaseous mixture is cooled in contact with the wall PA1. The constituent B is supposed at least partly condensable under the conditions of temperature and pressure thus encountered by the gaseous phase (I) and there is thus formed a liquid phase in contact with the exchange wall PA1 which fills over at least a portion of the thickness of the porous network of the exchange wall PA1.

Two cases can occur:

If the one or more constituent(s) other than B present in the mixture (constituent A) is or are not condensable, the liquid phase is formed by the practically pure constituent B. This is the case, for example, if the mixture concerned is a mixture of air and steam under conditions close to the ambient.

If a constituent other than B present in the mixture (constituent A) is at least partly condensable under the conditions of temperature and of pressure encountered in the course of the cooling in contact with the wall PA1, whilst being more volatile than the constituent B, the liquid phase obtained is formed by a mixture comprising the constituents A and B but richer in constituent B than the starting gaseous mixture.

In all cases, the gaseous phase (I) emerges from the compartment CE1 through the pipe 13 cooled and with a concentration of constituent B lower than on entry.

The cooling of the gaseous phase (I) in contact with the wall PA1 is ensured by making flow into the compartment CE2 a gaseous phase (II) which enters into the compartment CE2 through the pipe 14 at a lower temperature than the inflow temperature in the compartment CE1 of the gaseous phase (I).

The gaseous phase (II) reemerges from the compartment CE2 through the pipe 15 heated by heat exchange with the gaseous phase (I) through the wall PA1 entraining in the vapor state at least a portion of the constituent B which has condensed in the porous network of the exchange wall.

In the diagram of FIG. 2A there is only shown one exchange wall, but it is clear that in the process according to the invention, the device used to effect the exchange could run to a plurality of walls and compartments in alternation.

In the same way different geometries can be employed, and the walls can, for example, be flat or cylindrical or include undulations or ribs.

The one of more porous walls separating the gaseous phases (I) and (II) are characterized by a relatively high porosity, for example, higher than 50% and an average size of the pores which is generally very large with respect to the size of the molecules forming the gaseous phases (I) and (II), for example higher than 0.01 mm. Consequently, in the absence of a liquid phase no selectivity with respect to constituent B is observed, that is to say that a mixture of constituents A and B passing through the porous wall not filled with liquid under the effect of a difference of pressure reemerges with practically the same composition.

The presence of the liquid film of condensate is essential to effect a selective exchange of material.

It is consequently important for the one or more porous walls separating the gaseous phases (I) and (II) to be filled with liquid over at least a portion of the thickness over the whole surface in contact with each of the gaseous phases (I) and (II).

An example of an arrangement enabling such a condition to be ensured is shown diagramatically in FIG. 2C which takes up the basic arrangement of FIG. 2A.

The wall PA1 is vertical and is filled with liquid phase by capillarity. It communicates at its lower portion with a liquid phase reserve which is maintained at a constant level by removing through the pipe 16 the excess of condensed liquid phase which flows along the wall (flow shown diagrammatically by the arrow 17). Fluid-tightness is ensured at the lower portion of the wall PA1, in contact with the liquid phase reserve, by the sealing plate ET1, the height of the plate ET1 being greater than the height of the wall PA1 in contact with the liquid reserve.

Gaseous phases (I) and (II) are admitted into the compartment CE1 and CE2 at neighboring pressures.

A difference in pressure on each side of the wall is however acceptable as long as it remains less than the capillary over-pressure which maintains the condensed liquid phase in the pores, this over-pressure being all the higher as the average diameter of the pores is less, the surface tension of the condensed liquid phase is large and the angle of contact between said liquid phase and the material constituting the porous wall is small, said angle having always to be less than 90°.

Various materials may be used to construct the porous wall PA1.

The porous wall PA1 may be constructed, for example, by particle agglomeration.

These particles may be constituted of different materials: metals, ceramics, polymers and have different geometries, for example, substantially spherical particles of powder or elongated fibers.

The porous wall PA1 can thus be formed by sintering metal powders, and the metal used can for example, be copper, aluminum, nickel or steel.

It can also be formed by employing felts of unwoven fibers, and these fibers can, for example, be glass fibers or fibers of polymeric material, particularly fibers of textile polymer such as polyester.

To obtain high heat transfer coefficients, it is advantageous to reduce the thickness of a liquid film which is formed in the porous wall.

This may be obtained by limiting the thickness of the porous wall PA1 to a value less, for example, than 5 mm and preferably less than 2 mm. In this case and particularly if the porous material used is felt it is advantageous, to improve the mechanical resistance of the wall, to support it with a grid which may be metallic or of polymeric material, or a very porous support which does not fill with liquid.

The latter case is shown diagrammatically in FIG. 3.

In this case, the porous wall PA1 is obtained by juxtaposing a porous wall PAF wetted by the condensed liquid phase, of smaller thickness, preferably less than 2 mm, in contact with the gaseous phase (I) and a porous wall PAS unwetted by the condensed liquid phase.

The porous wall PAS is characterized by a high porosity and a large relative size of the pores, for example of the order of 1 mm. It is formed preferably of a material not wettable by the condensed liquid phase.

The porous wall can only be porous over a portion of its surface.

To improve the efficiency of the simultaneous exchange of heat and material effected between the gaseous phases (I) and (II), it is advantageous to use a multichannel device such as that which is shown diagrammatically in FIG. 4.

The device is constituted of flat separating plates which correspond to the previously described conditions.

In the compartments situated between these flat plates flow alternately the gaseous phase (I) and the gaseous phase (II).

The device comprises three exchange zones:

In the exchange zone ECC the two phases flow in countercurrent.

In the intake zone EA1 the gaseous phase (I) flows out through the orifices 30, 31 and 32, the adjacent orifices being plugged to avoid any passage of the gaseous phase (II). The gaseous phase (II) enters through the orifices 33, 34 and 35, the adjacent orifices being plugged to avoid any passage of the gaseous phase (I).

Into the intake zone EA2, the gaseous phase (I) enters through the orifices 36, 37 and 38, the adjacent orifices being plugged to avoid any passage of the gaseous phase (II). The gaseous phase (II) emerges through the orifices 39, 40 and 41, the adjacent orifices being plugged to avoid any passage of the gaseous phase (I).

The process according to the invention may be used to effect a simultaneous transfer of heat and water between two gases.

Different uses may be envisaged.

It is possible in particular to carry out such an exchange between cold and dry air coming from the ventilation of an air conditioned enclosure and hot and moist air which is sent to the enclosure before it is cooled in order to reduce the energy consumption of the cooling unit.

Such simultaneous exchange of heat and water may be envisaged, on the other hand, in the case of gaseous phases of very different natures.

Thus it is possible to perform an exchange of heat and water between a hot and humid natural gas before a cooling step intended to collect a liquid fraction and the cold and dry natural gas coming from the cooling step after separatin of the liquid fraction.

The condensable constituent may be other than water. Thus it is possible to recover a solvent present in the hot air of an enclosure in which this solvent in employed by carrying out an exchange with the cold air devoid of solvent sent to the enclosure.

A part of the gaseous phase (I) emerging from the exchange device cooled and impoverished in constituent B can be cooled outside the exchange device and sent back to the exchange device to form the gaseous phase (II).

In this case procedure is according to the diagram shown in FIG. 5.

The hot gas formed by the mixture of constituents A and B arrives through the pipe 45 into the exchange device DEC, in which it forms the gaseous phase (I). It emerges therefrom cooled, impoverished in constituent B and enriched in constituent A through the pipe 46. A part of the gas is removed through the pipe 47, the flow rate of evacuated gas being regulated by the valve V1. The fraction of unevacuated gas is expanded through the valve V2, cooled in the exchanger EC1 and sent back through the pipe 48 to the exchange device DEC in which it forms the gaseous phase (II). It emerges therefrom through the pipe 49 entraining at least a portion of the constituent B present in the initial mixture.

It is possible to increase the concentration of constituent B in the gas emerging through the pipe 49 by lowering the pressure, which enables the fraction of recycled gas to be reduced. In this case the maximum pressure deviation that the liquid film which is formed in the porous exchange walls of the exchange device DEC, can tolerate, must be respected taking into account the capillary overpressure.

Such an exchange method enables a mixture of condensable constituents to be fractionated during the exchange.

Figure 6:
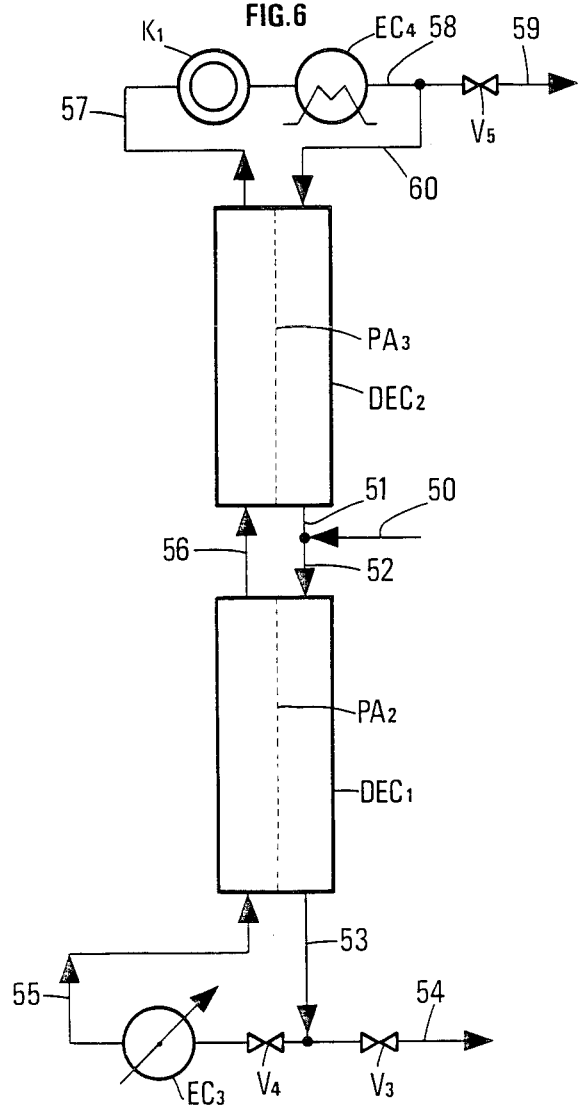
FIG. 6 is a diagram of a further use of the invention.

The diagram shown in FIG. 6 illustrates the arrangement which may be employed in this case. It is assumed to describe the separation method that the mixture only comprises two condensable constituents A and B, B being the constituent whose boiling point is highest, but the method can also be used to separate a mixture of more than two constituents into two distinct fractions.

The mixture of constituents A and B arrives through the pipe 50. It is mixed with the steam flow which arrives through the pipe 51 and the resulting mixture is sent through the pipe 52 to the exchange device DEC1. The exchange device DEC1 comprises porous walls as previously described, in which a liquid film is formed whose composition develops between the intake and the outlet of the vapor mixture which arrives through the pipe 52. This composition is enriched in constituent A progressively as the temperature diminishes and the vapor phase collected through the pipe 53 at the outlet from the exchange device DEC1 may be formed by the almost pure constituent A. A fraction of this vapor phase is removed through the pipe 54, the valve V3 permitting the removal flow rate to be regulated. the remaining fraction is expanded through the valve V4, cooled in the exchanger EC3 and then sent through the pipe 55 to the exchange device DEC1. It emerges from the exchange device DEC1, heated, enriched in constituent B, through the pipe 56, and is sent to the exchange device DEC2. The exchange device DEC2 comprises porous walls such as previously described in which a liquid film is formed whose composition develops between the inlet and the outlet of the vapor mixture which arives through the pipe 56. The composition of the gas is enriched in constituent B between the inlet 56 and the outlet 57 at the same time as the temperature increases. The vapor phase collected through the pipe 57 at the outlet of the exchange device DEC2 may thus be formed by the almost pure constituent B. This vapor phase is compressed in the compressor (overpresser) K1 then heated in the exchanger EC4. The heating step in the exchanger EC4 may not be necessary, the rise in temperature obtained in the course of the compression step in the compresser K1 being sometimes sufficient. A fraction of the compressed and heated vapor phase is evacuated, the valve V5 permitting the evacuation flow rate to be regulated. The remaining fraction is sent throught the pipe 60 to the exchange device DEC2. It emerges through the pipe 51 of the exchange device DEC2 cooled, impoverished in constituent B and enriched in constituent A.

It is thus possible to separate the mixture of constituents A and B which arrives through the pipe 50 into a fraction formed essentially by the constituent A, which is removed through the pipe 54, and a fraction formed essentially by the constituent B, which is removed through the pipe 59.

EXAMPLE 1

Example 1 is described in respect of FIG. 2C. There is introduced into the compartment CE1, through the pipe 12, a flow of 111.43 kg/h of moist air (fluid A) constituted by 100 kg/h of dry air and 11.43 kg/h of water, at the temperature of 55° C. Simultaneously into the compartment CE2, through the pipe 14, is sent a flow of 100.74 kg/h of moist air (fluid B) constituted by 100 kg/h of dry air and 0.74 kg/h of water, at the temperature of 15° C. so that the fluids A and B flow in countercurrent on each side of a porous diaphragm PA1 of which all the porosity is soaked with water in liquid form.

The diaphragm PA1 is constituted in this example by an unwoven felt having a thickness close to 1 millimeter constituted by cellulose fibres.

During the passage into the compartment CE1, the fluid A is cooled in contact with the diaphragm PA1 by abandoning by condensation on the latter a portion of the water that it contains whilst the fluid B, flowing in the compartment CE2, is heated and is charged with water in contact with the diaphragm PA1. The exchanges of heat and water between the fluids A and B are such that, on the one hand, the fluid A emerges through the pipe 13 at the temperature of 42° C. and is constituted by 100 kg/h dry air and 5.53 kg/h of water in steam form whilst 0.51 kg/h are removed in liquid form through the pipe 16 at the temperature of 28.5° C. and, on the other hand, the fluid B emerges that through the pipe 15 at the temperature of 43.6° C. and comprises 100 kg/h of dry air and 6.13 kg/h of water in vapor form.

In this example, the excess condensed water is removed from the compartment CE1 by gravity. To this end, a non-permeable wall ET1 avoids the passage of condensed water from the compartment CE1 wherein flows the liquid A to the compartment CE2 wherein flows the fluid B and thus permits its removal by gravity through the pipe 16 which comprises the features necessary for the maintenance of a liquid buffer at constant level at the lower part of the compartment CE1 in order to avoid removal of the fluid A through the pipe 16.

The heat energy transferred from fluid A to the fluid B is 4.4 kW of which about 4 kW and 0.4 kW result respectively from the heat of condensation of the water coming from the fluid A on the porous wall and the sensible heat due to the cooling of the fluid A. Simultaneously, the transfer of water from the fluid A to the fluid B amounts to 5.39 kg/h.

EXAMPLE 2

Example 2 is described with respect to the diagram of FIG. 6. In this example, the porous walls PA2 and PA3 of the exchange devices DEC1 and DEC2 are constituted by sintered nickel sheets of thickness equal to 0.8 millimeter.

Through the pipe 50 is sent a flow of 1 kg/h of a gaseous mixture of normal pentane (nC$_5$) and normal heptane (nC$_7$) whose composition in molar fractions is as follows:

nC$_5$:0.7 nC$_7$:0.3

After mixing with 6 kg/h of a gas coming from the exchange device DEC2 through the pipe 51, a mixture in vapor phase is obtained at a temperature of 70° C. and a pressure of 760 mm Hg, which is sent through the pipe 52 to the exchange device DEC1. At the outlet from the exchange device DEC1, there is collected through the pipe 53 pentane in vapor phase containing less 1% of heptane at a temperature of 35° C. A flow of 0.63 kg/h is taken by the pipe 54. The remaining fraction is cooled to 28° C. in the exchanger EC3 and sent in vapor phase at a pressure of 570 mm Hg through the pipe 55 into the exchange device DEC1. It emerges therefrom through the pipe 56 at a temperature of 67° C. and is sent to the exchange device DEC2. At the outlet of exchange device DEC2 there is collected through duct 57 heptane in vapor phase containing less than 1% of pentane at a temperature of 84° C. It is compressed to a pressure of 800 mm Hg in the compressor K1. The vapor phase is then sent into the exchanger EC4 whence it emerges through the pipe 58 at a temperature of 100° C.

A flow rate of 0.37 kg/h is taken up by the pipe 59. The remaining fraction is sent in vapor phase through the pipe 60 to the exchange device DEC2.

In this example the mixture of normal pentane and normal heptane was fractionated without it being necessary as in distillation to resort to a change in phase to obtain the reflux streams.

An essential condition in the embodiment illustrated by FIG. 6 is that, during each of the exchange steps, the fluid which is cooled should be at an average pressure higher than the fluid which is heated.

We claim:

1. Process for the simultaneous transfer of heat and matter from a relatively hot gaseous phase (I) to a relatively cold gaseous phase (II), the relatively hot gaseous phase (I) comprising at least two constituents A and B having different condensation temperatures, the condensation temperature of A being lower than the condensation temperature of B and at least the constituent B being at least in part condensable under the conditions of the process, said process comprising circulating the gaseous phase (I) in contact with the first face of an exchange wall permeable to at least the constituent B in the liquid state and circulating the gaseous phase (II) in contact wiht the second face of the porous exchange wall, in a direction substantially parallel and opposite that of the flow of the gaseous phase (I), the temperature of the gaseous phase (II) at the beginning of the contact being sufficiently low to permit the condensation of at least a fraction of the constituent B of the gaseous phase (I) and the maintenance of the resulting condensate in at least a part of the thickness of the porous portion of the exchange wall, the temperature of the gaseous phase (II) not however being too low to avoid total condensation of the constituents A and B of said gaseous phase (I) in the course of said contact, the conditions of pressure on each side of the wall being mutually adapted to permit said condensation of a fraction of the constituent B on the said first face and the vaporisation of said condensed fraction on said second face, and withdrawing separately the gaseous phase (I) of lowered temperature, of lowered concentration of constituent B and of increased concentration of constituent A and the gaseous phase (II) of increased temperature and increased concentration of constituent B.

2. Process according to claim 1, wherein the condensate is maintained in at least a portion of the thickness of the porous wall over the whole surface which separates the gaseous phase (I) from the gaseous phase (II).

3. Process according to claim 1, wherein the porous exchange wall is vertical and the condensed liquid phase which has not transferred through the wall, is allowed to fall back by gravity and removed, the liquid phase contained in the wall being renewed at least in part by capillarity.

4. Process according to claim 1, wherein the porous exchange wall comprises of an agglomerate of particles.

5. Process according to claim 1, wherein the porous exchange wall is constituted by fibers of polymeric material.

6. Process according to claim 1, wherein the average size of the pores of the porous exchange wall is greater than 0.01 mm.

7. Process according to claim 1, wherein the porosity of the porous exchange wall is greater than 50%.

8. Process according to claim 1, wherein the porous exchange wall has a thickness less than 5 mm.

9. Process according to claim 1, wherein the constituent B is water and the constituent A is a gas not condensable under the conditions of temperature and pressure encountered in the course of the exchange.

10. Process according to claim 1, wherein the constituents A and B are both condensable under the conditions of the process.

11. Process according to claim 10, further comprising dividing the gaseous phase (I) withdrawn into at least two fractions, further cooling a first fraction (Ia) of the divided gaseous phase (I) lowering the pressure of said first fraction, then circulating said first fraction in contact with the second face of the exchange wall, said first fraction thus constituting at least a portion of the gaseous phase (III), circulating the gaseous phase (II), after its contact with said second face of the exchange wall, in contact with the first face of a second exchange wall permeable at least to the constituent B in the liquid state, dividing the gaseous phase (III) obtained after said contact into at least two fractions, discharging a first fraction (IIIa) of said gaseous phase, heating and raising the pressure of a second fraction (IIIb) of said gaseous phase, then circulating said fraction (IIIb) in contact with the second face of the second exchange wall in a direction substantially parallel and opposite to that of the gaseous phase (II), the temperature of the gaseous phase (II) at the start of the contact with the first face of the second exchange wall being sufficiently low to permit the condensation of at least a fraction of the constituent B of the second gaseous fraction (IIIb) and maintenance of the resulting condensate in at least a portion of the thickness of the second exchange wall, said temperature not however being too low to avoid a total condensation of the constituents A and B of said second fraction of gaseous phase (IIIb) in the course of said contact, the conditions of pressure on each side of the second exchange wall being mutually adapted to permit said condensation of a fraction of the constituent B on said second face and vaporisation of said condensed fraction on said first face of said second wall, and mixing the gaseous phase (IV) resulting from said contact with the relatively hot gaseous phase (I) subjected to the process.

12. Process according to claim 1, wherein the gaseous phase (I) withdrawn is divided into at least two fractions, wherein a first fraction (Ia) of the divided gaseous phase (I) is further cooled and is then circulated in contact with the second face of the exchange wall, said first fraction thus constituting at least a portion of the gaseous phase (II), and discharging a second fraction (Ib) of the divided gaseous phase (I).

13. A process according to claim 1, wherein the wall separating the gaseous phases (I) and (II) is filled with liquid over at least a portion of the thickness over the whole surface in contact with each of the gaseous phases (I) and (II).

14. A process according to claim 1, wherein said condensed fraction of constituent B is only partly transferred to said second face of the wall, and the remainder flows along the first face of the exchange wall and is thereafter collected and discharged.

15. A process according to claim 14, wherein said porous exchange wall comprises an agglomeration of particles.

16. A process according to claim 15, wherein said particles comprise metals, ceramics, or polymers.

17. A process according to claim 16, wherein said particles comprise sintered metal powders.

18. A process according to claim 17, wherein said metals comprise copper, aluminum, nickel or steel.

19. A process according to claim 1, wherein said wall is constructed of an agglomeration of particles or fibers of polymeric materials.

20. A process according to claim 1, further comprising more than one exchange wall.

* * * * *